United States Patent [19]

Bevan

[11] 4,432,963

[45] Feb. 21, 1984

[54] RADIOGRAPHIC SCANNING AGENT

[75] Inventor: John A. Bevan, Cincinnati, Ohio

[73] Assignee: Mallinckrodt, Inc., St. Louis, Mo.

[21] Appl. No.: 225,151

[22] Filed: Jan. 14, 1981

Related U.S. Application Data

[62] Division of Ser. No. 929,472, Jul. 31, 1978, Pat. No. 4,247,534.

[51] Int. Cl.³ .................. A61K 43/00; A61K 49/00
[52] U.S. Cl. .............................. 424/1.1; 424/9
[58] Field of Search ........................ 424/1, 9

[56] References Cited

U.S. PATENT DOCUMENTS

| | | | |
|---|---|---|---|
| 3,683,080 | 8/1972 | Francis | 424/204 |
| 3,934,002 | 1/1976 | Haefele | 424/54 |
| 3,959,458 | 5/1976 | Agricola et al. | 424/52 |
| 3,965,254 | 6/1976 | Tofe et al. | 424/1 |
| 4,025,616 | 5/1977 | Haefele | 424/52 |
| 4,067,971 | 1/1978 | Francis et al. | 424/204 |
| 4,137,309 | 1/1979 | Van Duzee | 424/204 |
| 4,216,211 | 8/1980 | Francis | 424/204 |
| 4,216,212 | 8/1980 | Flora et al. | 424/204 |
| 4,229,427 | 10/1980 | Whitehouse | 424/1 |
| 4,232,000 | 11/1980 | Fawzi | 424/1 |
| 4,234,562 | 11/1980 | Tofe et al. | 424/1 |
| 4,247,534 | 1/1981 | Bevan | 424/1 |

OTHER PUBLICATIONS

Arnold et al, Abstract from Society of Nuclear Medicine, 26th Annual Meeting, Jun. 1979.
Bass et al, Abstract from Southeast Chapter, Meeting of the Society of Nuclear Medicine, Oct. 1980.
Bevan et al, J. Nucl. Med. 21 (1980): 967–970.
Domstad et al, Radiology, 136 (1980): 209–211.
Francis et al, J. Nucl. Med. 121 (1980): 1185 ∝ 1189.
Silberstein, Radiology, 136 (1980): 747–751.
Hayashi et al, Radioisotopes, 30 (1981) 38–39.

*Primary Examiner*—Christine M. Nucker
*Attorney, Agent, or Firm*—Bernard, Rothwell & Brown

[57] ABSTRACT

A composition and method for the preparation of a technetium-99m-based scanning agent are disclosed. The scanning agent is prepared from $^{99m}$Tc, in a +3, +4 and/or +5 oxidation state, and a methanehydroxydiphosphonate bone-seeking agent which carries the radionuclide to bone mineral. The methanehydroxydiphosphonate agent provides scan sharpness equivalent or superior to commercial scanning agents, and is superior for detecting myocardial infarcts, as compared with commercial scanning agents such as ethane-1-hydroxy-1,1-diphosphonate and methanediphosphonate.

9 Claims, No Drawings

RADIOGRAPHIC SCANNING AGENT

This is a division, of application Ser. No. 929,472, filed July 31, 1978, now U.S. Pat. No. 4,247,534.

TECHNICAL FIELD

This invention relates to a radiodiagnostic agents and more particularly to a composition and method for preparing a highly effective technetium-99m-based bone scanning agent.

For some time it has been recognized that conventional X-ray techniques are not entirely satisfactory for detecting many types of disorders at an early stage. One unfortunate deficiency of X-ray examination is the inability of that technique to detect skeletal metastases in their incipient stages when meaningful treatment is possible.

Early "bone scanning" work for detecting metastases was directed to the use of radioactive isotopes, especially the isotope fluorine-18 ($^{18}$F) which selectively migrates to the skeleton and especially to "active" sites thereon, such as the joints and tumor sites, where it exchanges with the hydroxyl group in calcium hydroxyapatite. $^{18}$F, however, has certain limitations due to its short half-life (110 minutes); viz., a very short "shelf life", as well as high energy emission which makes it unsuited for use with certain detection equipment, notably the Anger scintillation camera. Additionally, $^{18}$F requires very expensive equipment to prepare and is therefore quite unsuited for all but the most well equipped hospitals.

The strontium-85 isotope ($^{85}$Sr) has also been used in bone scanning. This radionuclide seeks the skeleton and exchanges with the calcium in calcium hydroxyapatite, particularly at actively metabolizing sites. Strontium-85 is at the opposite end of the usable half-life spectrum from $^{18}$F, having a half-life of 65 days. While this greatly increased half-life (compared with $^{18}$F) provides a desirable "shelf life", it requires that very long exposure times be used to achieve a usable scan, inasmuch as only small amounts can be administered since the total exposure of the patient to radiation must be minimized.

Because of the shortcomings with $^{18}$F and $^{85}$Sr, more recent work in nuclear medicine has been directed to technetium-99m ($^{99m}$Tc) which has a half-life of six hours. Interest in $^{99m}$Tc has also increased due to the availability of convenient commercial means for supplying this radionuclide in the hospital, as needed. A radionuclide solution in the oxidized pertechnetate ($^{99m}$TcO$_4^-$) form is obtained from commercial sources by elution with an isotonic saline solution from an alumina column. Organic solvent-extracted "Instant Technetium" is also available.

Pertechnetate from commercial sources is in what is believed to be the +7 oxidation state, which does not combine with bone mineral-seeking agents to provide bone scans, and the like. This problem is easily overcome by reducing the pertechnetate to what is believed to be the +3, +4 and/or +5 oxidation state, referred to hereinafter as technetium-99m or $^{99m}$Tc.

Technetium-99m is different from either $^{18}$F or $^{85}$Sr in that it does not specifically seek or react with the skeleton. Its use, therefore, depends on compounding or complexing $^{99m}$Tc with bone mineral-seeking agents.

In general, $^{99m}$Tc-labeled bone scanning agents are prepared by admixing a pertechnetate-99m isotonic saline solution with a pertechnetate reducing agent such as the stannous, ferrous, titanous or chromous salt of sulfuric or hydrochloric acid, and the desired carrier agent for targeting bone mineral. For example, U.S. Pat. No. 4,016,249, issued Apr. 5, 1977, teaches a means for targeting bone mineral with radioactive technetium by using $^{99m}$Tc in combination with certain soluble phosphates. Liquid, dry powder mixture and freeze-dried bone scanning kits containing phosphate or phosphonate bone seeking agents are currently being marketed by various manufacturers.

BACKGROUND ART

U.S. Pat. No. 3,983,227, Tofe and Francis, discloses the use of dry powder mixtures of reducing salts with a great variety of organophosphonate bone-seeking carriers to prepare bone scanning agents from radioactive pertechnetate solutions. The methanehydroxydiphosphonates used herein are included among the myriad types of phosphonates taught by patentees to be useful in dry mixtures suitable for the preparation of bone scanning agents.

The references relating to bone mineral-seeking agents and their use with $^{99m}$Tc do not suggest the special advantages of methanehydroxydiphosphonate in radiodiagnostic products used for targeting bone mineral. For example, the reference which mentions methanehydroxydiphosphonate in bone scanning agents (U.S. Pat. No. 3,983,227) does so only as part of a rather general listing of a variety of organophosphonates, and only in the context of the powder mixture-type of product.

It has now been discovered that methanehydroxydiphosphonate, when used in the manner disclosed herein, unexpectedly provides both sharp bone mineral images and excellent lesion detection. Moreover, the methanehydroxydiphosphonates are superior to the other well-known organic phosphonates when used with $^{99m}$Tc to image myocardial infarcts which, in the acute phase, are associated with high levels of calcium.

DISCLOSURE OF INVENTION

Radiodiagnostic agents comprising $^{99m}$Tc and various organophosphonate or inorganic phosphate bone seeking agents are currently used in hospitals. It has now been discovered that the methanehydroxydiphosphonate bone mineral-seeking agent disclosed herein is unique in that it unexpectedly provides the dual benefits of sharp radiographic imaging and excellent lesion detection when used with $^{99m}$Tc. Moreover, the methanehydroxydiphosphonate agent can also be used with $^{99m}$Tc for detecting soft tissue calcification (e.g., myocardial infarct imaging) in the manner of the inorganic phosphate radiodiagnostic agents.

Radionuclide uptake in uncalcified soft tissue is usually a major problem with scanning agents prepared from reducing metals/pertechnetate/organophosphonates, since excessive soft tissue uptake, especially in the liver, can obscure large portions of the skeletal scan. Past efforts to minimize soft tissue uptake have centered mainly on using minimal amounts of the reducing metal, and the ratio of organophosphonate:reducing metal in many commercial products is typically 10–40 to 1.

As disclosed more fully hereinafter, to achieve the special advantages of the present invention it is necessary to use somewhat smaller amounts of the methanehydroxydiphosphonate than are used with various other organophosphonates in radiodiagnostics. By using said smaller amounts of this diphosphonate, undesirable deposition of the $^{99m}$Tc in the liver is avoided, and the sharpness/detection/M.I. imaging advantages are secured without the scan being obscured by liver uptake.

BEST MODE

The present invention is based on the use of methanehydroxydiphosphonic acid (and the water-soluble salts and hydrolyzable esters thereof) as a bone mineral-seeking agent to target bone mineral with radioactive technetium. The methanehydroxydiphosphonate is conveniently supplied in a freeze-dried composition, said composition providing both a reducing metal ion for reducing pertechnetate (TcO$_4^-$) to a lower valence (oxidation state) and the methanehydroxydiphosphonate moiety for carrying the lower-valent technetium to bone mineral. In an optional mode, the composition can contain a noninterfering amount of a stabilizer material to inhibit or reduce the oxidation of the pertechnetate reducing agent (e.g., oxidation of Sn$^{+2}$ to Sn$^{+4}$) during storage and/or to inhibit or prevent the reoxidation of reduced technetium and/or formation of technetium-labeled impurities during use.

In another product form, the methanehydroxydiphosphonate can be supplied in an aqueous solution in combination with a technetium reducing agent. Since the technetium reducing agent is preferably a soluble metal ion which is readily oxidized, it is highly preferred that such aqueous compositions contain a stabilizer material of the type mentioned above.

In another mode, the methanehydroxydiphosphonate can be provided as a metal compound, i.e., in chemical combination with the reducing metal for the technetium. Included among such compounds are the water-soluble stannous methanehydroxydiphosphonates, water-soluble ferrous methanehydroxydiphosphonates, water-soluble chromous methanehydroxydiphosphonates, water-soluble titanous methanehydroxydiphosphonates, and the like. When such combined reducing metal/bone mineral-seeking compounds are used in the preparation of a radiodiagnostic agent from technetium, it is preferred that some excess methanehydroxydiphosphonate over that used to prepare the metal-methanehydroxydiphosphonate compound, itself, be present to ensure good bone mineral imaging. However, the amount of said excess of methanehydroxydiphosphonate does not exceed that specified hereinafter, so that undesired liver uptake is avoided. Stabilizers of the type disclosed above are also useful in such compositions.

In yet another product form, the compositions of the present invention comprise simple mixtures of technetium reducing agent, methanehydroxydiphosphonate and, optionally, a stabilizer.

Methanehydroxydiphosphonate

Methanehydroxydiphosphonic acid and its related salts and esters can be prepared, for example, by the reaction of phosgene with an alkali metal dialkyl phosphite. A complete description and methods of preparation are found in U.S. Pat. No. 3,422,137, Quimby, granted Jan. 14, 1969, the disclosures of which are incorporated herein by reference. Only those esters which hydrolyze under use conditions to the free acid or anion form can be used herein.

Methanehydroxydiphosphoric acid has the molecular formula HC(OH)(PO$_3$H$_2$)$_2$. While the free acid or any pharmaceutically-acceptable, water-soluble salt or hydrolyzable ester of methanehydroxydiphosphonic acid can be used in the practice of this invention, the alkali metal (especially sodium) and the ammonium salts are preferred. These compounds are fully described in the Quimby patent, above.

Representative examples of methanehydroxydiphosphonates useful herein include the following salts and esters: monosodium, disodium, trisodium, tetrasodium, and mixtures thereof; monopotassium, dipotassium, tripotassium, tetrapotassium, and mixtures thereof; mono-ammonium, di-ammonium, tri-ammonium, tetra-ammonium, and mixtures thereof; mono-, bis-, tris-, and tetrakis (tetraalkyl ammonium) wherein alkyl is, for example, methyl, ethyl or propyl; monomethyl; monoethyl; mono-, bis-, tris- and tetrakis-(alkanolammonium), e.g., mono-(triethanolammonium), bis-(triethanolammonium), tris-(triethanolammonium), and tetrakis-(triethanolammonium); and mixtures of the foregoing methanehydroxydiphosphonates which are soluble or are hydrolyzable in water at the usage concentrations of the present invention. The "free acid" form methanehydroxydiphosphonic acid can also be used.

The sodium salts of methanehydroxydiphosphonic acid and the free acid, itself, are most preferred for use herein.

Pertechnetate Reducing Agent

As used herein the term "pertechnetate reducing agent" includes compounds, complexes, or the like, comprising a reducing ion capable of reducing heptavalent technetium (TcO$_4^-$) to trivalent, tetravalent and/or pentavalent technetium. Free metals such as tin are also known for use as pertechnetate reducing agents, although undissolved metal must be removed from the scanning solution prior to injection into the patient. Thus, it is more convenient to use metal compounds which provide a reducing metal cation in injectable, water-soluble form.

Suitable pertechnetate reducing agents include metallic salts of sulfuric acid and hydrochloric acid, such as stannous chloride, chromous chloride and ferrous sulfate. Other agents capable of reducing pertechnetate-99m include, for example, titanous halides, acid-thiosulfates, acid-hydrogen-sulfates, iron colloids, and acid-borohydrides. U.S. Pat. Nos. 3,735,001 granted May 22, 1973; 3,863,004 granted Jan. 28, 1975; 3,466,361 granted Sept. 9, 1969; 3,720,761 granted Mar. 13, 1973; 3,723,612 granted Mar. 27, 1973; 3,725,295 granted Apr. 3, 1973; 3,803,299 granted Apr. 9, 1974; and 3,749,556 granted July 31, 1973 (all incorporated herein by reference) disclose various pertechnetate reducing agents comprising reducing ions capable of reducing heptavalent pertechnetate to appropriate lower valence states.

Water-soluble stannous (Sn$^{+2}$) compounds, especially stannous chloride, are preferred for use as the pertechnetate reducing agent herein. Stannous bromide, fluoride and sulfate can also be used. Stannous salts of organic acids, such as stannous tartrate or maleate, can be used, as can the stannous salt of methanehydroxydiphosphonic acid.

Optional Stabilizer

The compositions herein optionally, and preferably, contain a stabilizing amount of a stabilizer material to prevent or inhibit the oxidation of the pertechnetate reducing agent (e.g., oxidation of Sn$^{+2}$ to Sn$^{+4}$) during storage and/or to inhibit or reduce the reoxidation of reduced technetium-99m and/or to reduce the formation of technetium-labeled impurities which may form during use of the compositions.

The stabilizers used herein are characterized by their toxicological acceptability under the conditions of use, their ability to stabilize the product for a reasonable period of storage and/or under usage conditions, and by their substantial non-interference with the delivery of the technetium radionuclide to bone mineral.

Stabilizers which meet the foregoing requirements and which are quite suitable for intravenous injection include gentisic acid and its water-soluble salts and esters, ascorbic acid and its water-soluble salts and esters, and erythorbic acid and its water-soluble salts and esters. Gentisic acid, ascorbic acid and erythorbic acid are all known, commercially-available materials. The sodium salts of these acids are all avaiable, quite water-soluble, and preferred for use herein.

As is known in the literature, stabilizer materials such as ascorbic acid can chelate/complex with technetium and cause it to be deposited in uncalcified soft tissue. Since the practitioner of the present invention will wish to avoid all unnecessary deposition in soft tissue, it will be appreciated that the amount of stabilizer material optionally used in the present compositions should not be so great as to overshadow the bone-directing effect of the methanehydroxydiphosphonate, thereby interfering with the bone scan. Appropriate, non-interfering amounts of stabilizer materials for use in combination with the methanehydroxydiphosphonate are disclosed in more detail, hereinafter.

Methods

The compositions of the present invention are intended for intravenous injection into humans or lower animals. Accordingly, appropriate manufacturing and operating conditions are employed to provide suitably sterile, pyrogen-free compositions.

It has been discovered that dosages of methanehydroxydiphosphonate above about 0.1 mg. per kilogram of body weight (mg./kg.) are excessive for a radiodiagnostic product intended for bone mineral scanning, inasmuch as liver uptake of the technetium radionuclide becomes excessive and scan quality suffers. Preferably, the total amount of methanehydroxydiphosphonate bone mineral-seeking agent used per scan does not exceed about 0.1 mg./kg., and is more preferably in the range of about 0.001 mg./kg. to about 0.05 mg./kg.; most preferably about 0.4 mg./70 kg.

As disclosed hereinabove, undesirable soft tissue uptake can be further minimized by avoiding excess amounts of the pertechnetate reducing agent. The weight ratio of methanehydroxydiphosphonate bone mineral-seeking agent to technetium reducing agent is generally in the range from about 8:1 to about 30:1, more preferably about 10:1 to about 13:1, most preferably about 12:1.

As a further means for avoiding undesirable soft tissue uptake of technetium, the weight ratio of methanehydroxydiphosphonate:optional stabilizer material is kept in the range from about 20:1 to about 1:1, more preferably about 2:1 to about 20:1, most preferably about 3:1 to about 5:1.

The compositions of the present invention can be prepared by simply dry mixing the technetium reducing agent and the methanehydroxydiphosphonate agent. The optional stabilizer can also be dry-blended into such mixtures, as can additional, non-interfering agents such as sodium chloride. Conveniently, such compositions are provided in mixing vials fitted with a rubber septum for ease-of-mixing with a pertechnetate solution and ease-of-use in the hospital. The vials are preferably nitrogen-filled as an added protection against oxidation of the technetium reducing agent on storage.

In an alternate mode, the compositions herein can be provided in freeze-dried form. Such compositions are prepared by co-dissolving the methanehydroxydiphosphonate agent and the technetium reducing agent in an aqueous solution, together with any desired optional stabilizers, and freeze-drying the composition using standard equipment. Preferably, sterile, deoxygenated water is used in processing and the product is stored under nitrogen. Although somewhat more complicated to manufacture than the dry mixture product, the freeze-dried product offers the advantage that water-insoluble particulate matter which might be present in the raw materials can be removed by filtration prior to the freeze drying step.

In another mode, the compositions herein can be provided as aqueous solutions in sterile, pyrogen-free water. Preferably, the water is deoxygenated and the composition is stored under nitrogen, thereby minimizing undesirable oxidation of the pertechnetate reducing agent on storage. Since the reducing agent is more prone to oxidize in solution than in the dry powder and freeze-dried composition forms, it is preferred that aqueous compositions contain a stabilizer.

Compositions of the present type wherein the weight ratio of methanehydroxydiphosphonate:technetium reducing agent is in the range of about 8:1 to about 15:1, more preferably about 10:1 to about 13:1, are preferred.

Stabilized compositions wherein the weight ratio of methanehydroxydiphosphonate bone mineral-seeking agent:stabilizer is in the range of from about 2:1 to about 20:1, most preferably about 2:1 to about 10:1, and wherein the weight ratio of methanehydroxydiphosphonate bone mineral-seeking agent:reducing agent is in the range of from about 8:1 to about 13:1 are highly preferred.

Preferred compositions herein for preparing excellent skeleton and infarct scans using commercial pertechnetate-99m sources comprise from about 0.1 mg. to about 0.5 mg. of a water-soluble stannous salt selected from stannous chloride, stannous sulfate, stannous maleate, and stannous tartrate; and from about 1 mg. to about 5 mg. of a sodium salt of methanehydroxydiphosphonate.

Preferred, stabilized compositions comprise from about 0.1 mg. to about 0.5 mg. of the stannous reducing agent; from about 0.25 mg. to about 1.0 mg. of the gentisate or ascorbate stabilizer; and from about 1 mg. to about 5 mg. of the methanehydroxydiphosphonate agent.

Compositions of the foregoing type are characterized by a physiologically-acceptable in-use solution pH in the range from about 3.5 to about 8, and, in the main, fall within a preferred pH range of 4 to about 6.

In use, the compositions are dissolved with a pertechnetate-99m isotonic solution from a commercial technetium source to yield a bone mineral scanning agent suitable for intravenous injection. The stability of such scanning agents is ample under ordinary hospital conditions. Administration is preferably done within about eight hours after addition of the pertechnetate solution. Preferably, the concentration of reagents and technetium radionuclide is sufficient that about 1 ml. of the solution is used in an adult of about 50–100 kg. body weight. One ml. of solution is preferably injected intravenously over a period of about 30 seconds. The total dosage of radionuclide for a sharp skeletal or myocardial infarct scan ranges from about 5 millicuries to about 30 mCi, preferably from about 10 mCi to about 20 mCi. Since the methanehydroxydiphosphonate agent provides such sharp scan quality and minimizes soft tissue uptake, the total exposure of the patient to radionuclide can be minimized, as compared with scanning agents which employ different types of bone mineral-seeking agents.

In an alternate mode, the methanehydroxydiphosphonate can be present in the solution to elute the $TcO_4^-$ from the source, whereafter the reduction can be effected with the reducing agent.

The actual identity of the water-soluble reaction product formed by the $^{99m}Tc$/methanehydroxydiphosphonate/reducing agent mixture and introduced into the body is not known with certainty. Water-soluble compounds including $^{99m}Tc$-methanehydroxydiphosphonate, or that bipartite species in combination with the reducing agent (tin, iron, chromium or titanium) as a soluble tripartite species, are probably present in solution.

INDUSTRIAL APPICABILITY

The following examples illustrate the industrial applicability of this invention, but are not intended to be limiting thereof.

EXAMPLE I

| Ingredient | Milligrams |
| --- | --- |
| Methanehydroxydiphosphonic acid | 2.0 |
| Stannous chloride | 0.16 |
| Sodium chloride | 25.0 |

The composition of Example I is prepared by dry blending the three ingredients. The composition is stored under nitrogen in a 5-ml. vial, fitted with a rubber septum. On addition of about 5 ml. of a pertechnetate-99m solution from a commercial technetium source, and thorough shaking, the composition dissolves to yield a skeletal scanning agent suitable for intravenous injection into a human or animal patient. Preferably, about 1 ml. of the solution is used in an adult or animal subject of about 50–100 kg. body weight and is injected slowly, over a period of about 30 seconds.

The composition of Example I is modified by replacing the stannous chloride with an equivalent amount of stannous sulfate, ferrous chloride, titanous chloride and chromous chloride, respectively, and equivalent results are secured.

The composition of Example I is modified by replacing the methanehydroxydiphosphonic acid with an equivalent amount of the monosodium, disodium, trisodium and tetrasodium salts of methanehydroxydiphosphonic acid, and mixtures thereof, respectively. Equivalent results are secured.

The composition of Example I is adjusted to pH's over the range of about 3.0 to about 8.0 without substantially altering its efficacy as a bone-seeking agent.

EXAMPLE II

Methanehydroxydiphosphonate, mixture of di-, and trisodium salts (2.0 mg.), stannous chloride (0.16 mg.), and sodium gentisate stabilizer (0.50 mg.) are dissolved in 1 ml. of deoxygenated water at room temperature. The aqueous solution is filtered through a Millipore filter and freeze-dried on a commercial apparatus.

The freeze-dried powder prepared in the foregoing manner is admixed with about 5 ml. of a pertechnetate-99m solution from a commercial source. The freeze-dried powder dissolves readily and a stable skeletal scanning agent suitable for intravenous use is secured.

EXAMPLE III

Methanehydroxydiphosphonate, mixture of di-, trisodium salts (2.0 mg.), stannous chloride (0.16 mg.), and sodium ascorbate stabilizer (0.50 mg.) are dissolved in 1 ml. of deoxygenated water at room temperature. The aqueous solution is filtered through a Millipore filter and freeze-dried on a commercial apparatus.

The freeze-dried powder prepared in the foregoing manner is admixed with about 5 ml. of a pertechnetate-99m solution from a commercial source. The freeze-dried powder dissolves readily and a stable skeletal scanning agent suitable for intravenous use is secured.

EXAMPLE IV

A stabilized composition for imaging the skeleton as well as calcified soft tissue, especially myocardial infarcts, is as follows.

| Ingredient | Milligrams/vial |
| --- | --- |
| MHDP* | 2.0 |
| $SnCl_2$ | 0.16 |
| Gentisic acid | 0.50 |
| NaCl | 26.5 |

*Mixture of sodium salts of methanehydroxydiphosphonic acid.

The ingredients are dry mixed. Five mls. of eluate from a commercial pertechnetate source are added to one vial of the composition of Example IV to provide sufficient solution for 5 infarct scans. The composition can be used in like manner for bone scanning.

EXAMPLE V

Water-soluble stannous methanehydroxydiphosphonate is prepared by admixing equal volumes of a 0.02 molar aqueous solution of methanehydroxydiphosphonic acid and 0.012 molar aqueous, deoxygenated stannous chloride solution, under nitrogen. The combined solutions are stirred for one hour under nitrogen, filtered to remove insolubles and freeze-dried to yield water-soluble stannous methanehydroxydiphosphonate.

In like manner, 0.012 molar aqueous solutions of chromous chloride, titanous chloride and ferrous chloride are individually admixed with 0.02 molar aqueous solutions of methanehydroxydiphosphonic acid and the respective water-soluble chromous, titanous and ferrous methanehydroxydiphosphonates are secured.

A bone scanning agent which employs the metal methanehydroxydiphosphonates of the foregoing type is as follows.

| Ingredient | Milligrams/vial |
| --- | --- |
| Stannous methanehydroxydiphosphonate | 1.0 |
| MHDP* | 0.5 |
| Sodium ascorbate | 0.3 |

*Mixture of sodium salts of methanehydroxydiphosphonic acid.

The ingredients are dry mixed and used in the manner of Example IV as a bone scanning agent.

In like manner, water-soluble chromous methanehydroxydiphosphonate, titanous methanehydroxydiphosphonate and ferrous methanehydroxydiphosphonate can replace stannous methanehydroxydiphosphonate in a bone scanning agent.

What is claimed is:

1. Water-soluble stannous methanehydroxydiphosphonate.
2. Water-soluble ferrous methanehydroxydiphosphonate.
3. Water-soluble chromous methanehydroxydiphosphonate.
4. Water-soluble titanous methanehydroxydiphosphonate.
5. The water-soluble composition of matter $^{99m}$Tc-methanehydroxydiphosphonate.
6. The water-soluble composition of matter $^{99m}$Tc-methanehydroxydiphosphonate-tin.
7. The water-soluble composition of matter $^{99m}$Tc-methanehydroxydiphosphonate-iron.
8. The water-soluble composition of matter $^{99m}$Tc-methanehydroxydiphosphonate-chromium.
9. The water-soluble composition of matter $^{99m}$Tc-methanehydroxydiphosphonate-titanium.

* * * * *